(12) United States Patent
Griffiths et al.

(10) Patent No.: US 8,769,868 B2
(45) Date of Patent: Jul. 8, 2014

(54) COMPOSITIONS COMPRISING EICOSAPENTAENOIC ACID SUITABLE FOR HIGH PURIFICATION

(75) Inventors: Hywel David Griffiths, Auckland (NZ); Karl Thomas Geiringer, Wellington (NZ); Mark Humphrey Dines, Auckland (NZ)

(73) Assignee: Photonz Corporation Limited, Auckland (NZ)

( * ) Notice: Subject to any disclaimer, the term of this patent is extended or adjusted under 35 U.S.C. 154(b) by 0 days.

(21) Appl. No.: 13/702,616

(22) PCT Filed: Jun. 9, 2011

(86) PCT No.: PCT/NZ2011/000100
§ 371 (c)(1),
(2), (4) Date: Feb. 7, 2013

(87) PCT Pub. No.: WO2011/155852
PCT Pub. Date: Dec. 15, 2011

(65) Prior Publication Data
US 2013/0131173 A1    May 23, 2013

(30) Foreign Application Priority Data

Jun. 9, 2010  (NZ) .................................. 586018
Oct. 29, 2010  (NZ) .................................. 588914

(51) Int. Cl.
*A01H 13/00* (2006.01)

(52) U.S. Cl.
USPC ............................. 47/1.4; 424/683; 424/684

(58) Field of Classification Search
USPC ...................................... 47/1.4; 424/683, 684
See application file for complete search history.

(56) References Cited

U.S. PATENT DOCUMENTS

| 5,130,242 A | 7/1992 | Barclay |
| 5,340,594 A | 8/1994 | Barclay |
| 5,567,732 A | 10/1996 | Kyle et al. |
| 6,664,405 B2 | 12/2003 | Lee |
| 2010/0021555 A1 | 1/2010 | Geiringer et al. |
| 2010/0069492 A1 | 3/2010 | Geiringen et al. |

OTHER PUBLICATIONS

Wen et al., High cell density culture of the diatom *Nitzschia laevis* for eicospentaenoic acid production: fed-batch development, 2002, Process Biochemistry, vol. 37, pp. 1447-1453.*
Wen, Z. 2011, "A high yield and productivity strategy for eicosapentaenoic acid production by the diatom *Nitzschia laevis* in heterotrophic culture"—thesis published by the University of Hong Kong.
Tan, C. K. et al., "Screening of diatoms for heterotrophic eicosapentaenoic acid production", Journal of Applied Phycology, 1996, vol. 8 pp. 59-64.
Wen, Z.Y., et al. "A perfusion-cell bleeding culture strategy for enhancing the productivity of eicosapentaenoic acid by *Nitzschia laevis*", Appl. Microbiol. Biotechnol., 2001, vol. 57, 316-322.
Cao, X., et al., "Effects of nutritional factors on the growth and heterotrophic eicosapentaenoic acid production of diatom *Nitzschia laevis*", J. Ocean Univ. Chin., 2008, vol. 7(3), pp. 333-338.
Supplementary European Search Report, European Application No. 11792727.7-1401/2580342, PCT/NZ2011000100, Applicant: Photonz Corporation Limited, Date of Mailing: Oct. 14, 2013, pp. 1-3.
Wen Zhi-You, et al.,"Heterotrphic Production of Eicosapentaenoic Acid by Microalage,", Biotechnology Advances, Elsevier Science, Inc., Jul. 1, 2003, pp. 273-294.
Wen Zhi-You, et al., "Perfusion Culture of the Diatom *Nitzschia laevis* for Ultra-High Yield of Eicosapentaenoic Acid," Process Biochemistry, Elsevier Science, Inc., Dec. 2, 2002, pp. 523-529.

* cited by examiner

*Primary Examiner* — Ali Soroush
(74) *Attorney, Agent, or Firm* — Cesari and McKenna, LLP

(57) ABSTRACT

The invention relates to a microbial biomass composition produced from a heterotrophic fermentation whose fatty acid profile exhibits: an eicosapentaenoic acid (EPA) to arachidonic acid (ARA) ratio of about 11:1 or more; an EPA to total co-concentrating fatty acid ratio of about 8:1 or more, extract compositions, and methods of producing such compositions.

14 Claims, 1 Drawing Sheet

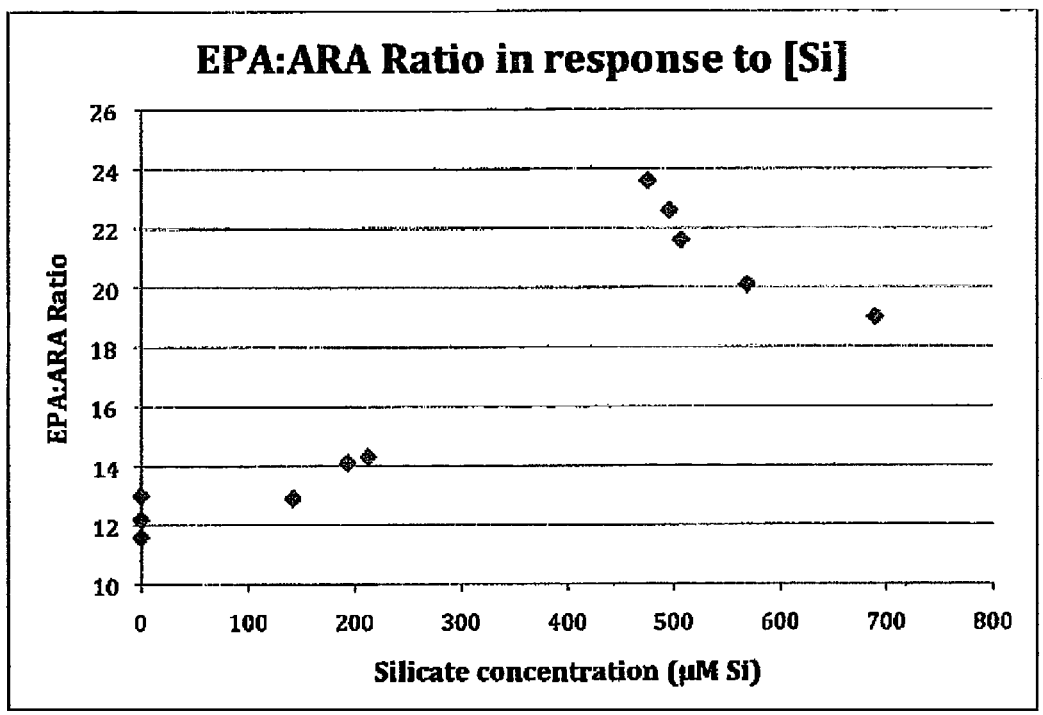

COMPOSITIONS COMPRISING EICOSAPENTAENOIC ACID SUITABLE FOR HIGH PURIFICATION

CROSS-REFERENCE TO RELATED APPLICATIONS

This application is the National Stage of International Application No. PCT/NZ2011/000100, filed on Jun. 9, 2011, which claims the benefit of the priority date of New Zealand Application No. 586018, filed on Jun. 9, 2010 and New Zealand Application No. 588914, filed on Oct. 29, 2010. The contents of these applications are hereby incorporated by reference their entirety.

FIELD OF THE INVENTION

The field of this invention relates to compositions containing eicosapentaenoic acid that are suited to concentration and purification for pharmaceutical and industrial use, and methods and processes for the production of such compositions.

BACKGROUND TO THE INVENTION

Pharmaceuticals containing very long chain omega-3 fatty acids (VLC n-3 FA) are currently used to treat hundreds of thousands, and potentially will soon be used to treat, millions of patients who have, or are at risk of, developing cardiovascular disease. In addition, the use of these substances in pharmaceuticals to treat other conditions is under consideration.

VLC n-3 FA cannot be chemically synthesised de novo economically, therefore must be extracted from a biological source. With such sources, the bulk of the VLC n-3 FA will be found in cellular structures such as membranes or lipid bodies and hence will be associated with other molecules which may not be desired in a pharmaceutical product. In these cases the VLC n-3 FA will need to be extracted and purified to some degree before use.

Pharmaceutical manufacturers currently rely on fish as the source of VLF n-3 FA for production of drug substances. Exclusive reliance on fish oil for such purposes, however, carries a number of serious risks to pharmaceutical manufacturers and drug companies as well as potentially to patients receiving such medications. Such risks include, but are not limited to, those associated with potential supply shortages, which may be financially devastating to drug companies as well as negatively affect patients who rely on medications for their well being.

Eicosapentaenoic acid (EPA) is a VLC n-3 FA used as an active metabolite in drug substances. To allow therapeutics to be well tolerated by patients and achieve the levels of bioavailability required for the drug to produce its desired effects it is desirable that EPA is delivered in a highly purified form.

Producing pharmaceuticals or other therapeutic agents from fish oil is complex and there is potential for the composition of the end product to become altered due to inherent variability in the fish capture and or breeding and fish oil production process. There are also widespread concerns over the long term sustainability of wild fish stocks and aquaculture.

There is an acute need therefore, for alternative sources of EPA to fish oil which are amenable to the subsequent degree of purification of EPA desirable for its use in the production of pharmaceuticals or other therapeutic agents.

Current industrial processes for the production of high-purity EPA often perform a concentration step (in which short chain fatty acids and saturated fatty acids are removed from the mixture) followed by a purification step (in which compounds with physiochemical and structural similarity to EPA are removed).

The former process is often incapable of separating EPA from arachidonic acid (ARA) and other fatty acids comprising 20 carbons or more and which contain at least one double bond (co-concentrating fatty acids), thus the development of sources of EPA other than fish oil in which the content of these fatty acids is minimised is highly desirable.

Purification processes experience difficulty in separating molecules which are physiochemically and structurally similar to EPA. The most common molecular species found naturally with greatest similarity to EPA is another fatty acid, ARA. The development of sources of EPA other than fish oil which are substantially free of such molecules is therefore highly desirable.

Such sources should ideally also be free of fatty acids that are not found in appreciable concentrations, or at all, in the diet of mainstream human populations as their biological activity may not be well characterised making them unsuitable for pharmaceutical use. This is especially so when said fatty acids are of sufficient structural or physiochemical similarity to EPA that they would be difficult to purify from EPA.

EPA is synthesised as part of a dual parallel biosynthetic pathway that produces omega-3 and omega-6 fatty acids (for example see Damude and Kinney (*Lipids* 42: 179-185, 2007)). Many of the enzymes are shared between pathways and will act upon either the omega-3 or omega-6 form of a fatty acid, thus the products of the omega-6 pathway are commonly found alongside those of the omega-3 pathway. In particular ARA is commonly found alongside EPA. Each step of the synthetic pathway is catalysed by separate enzymes and it is not uncommon for pathway intermediates to accumulate, these will include fatty acids with a lower number of double bonds but the same number of carbon molecules. ARA and EPA may also be substrates for further elongation and desaturation into fatty acids such as docosapentaenoic acid (DPA) and docosahexaenoic acid (DHA). It is therefore unsurprising that organisms which contain EPA generally also contain significant amounts of ARA and co-concentrating fatty acids.

Thus, there is a need in the art to provide EPA in a form that is amenable to high grade purification for therapeutic use and in plentiful supply. In particular there is a need for provision of EPA in a form that is separable from other fatty acids that are physiochemically and structurally similar to EPA (for example ARA).

SUMMARY OF THE INVENTION

In a first aspect the invention provides a microbial biomass produced from a heterotrophic fermentation, the biomass having a fatty acid profile exhibiting:
- an eicosapentaenoic acid (EPA) to arachidonic acid (ARA) ratio of about 11:1 or more; and
- an EPA to total co-concentrating fatty acid ratio of about 8:1 or more.

Preferably no juniperonic acid (JPA) and/or sciadonic acid is/are present in the co-concentrating fatty acids.

Preferably the microbial biomass is a microalgal biomass.

Preferably the microalgal biomass is a *Nitzschia laevis* biomass.

In a second aspect the invention provides a process for producing a microbial biomass whose fatty acid profile exhibits an eicosapentaenoic acid (EPA) to arachidonic acid (ARA)

ratio of about 11:1 or more, and an EPA to total co-concentrating fatty acid ratio of about 8:1 or more, comprising the steps of:
(i) heterotrophically culturing a microorganism; and
(ii) recovering said microbial biomass.

Preferably the microorganism is cultured in a culture medium under non-limiting carbon provision.

Preferably the microorganism is cultured in a culture medium under non-limiting nitrogen and non-limiting phosphate provision.

Preferably the microorganism is microalgal.

Preferably the microorganism is a diatom.

Preferably where the microorganism is a diatom, the microorganism is cultured in a culture medium under non-limiting bioavailable silicon provision.

Preferably the process further comprises the step of extracting fatty acids from said biomass to yield a fatty acid composition.

Preferably the process further comprises the step of enriching the fatty acid composition in EPA or purifying EPA from the fatty acid composition to yield an enriched or purified fatty acid composition.

In a third aspect the invention provides a microbial biomass obtainable or obtained by the process of the second aspect.

In a fourth aspect the invention provides fatty acid composition obtained or obtainable by the process of the second aspect.

Preferably the level of EPA in said fatty acid composition is at least 5% by weight of the total fatty acids in the composition.

In a fifth aspect the invention provides an enriched or purified fatty acid composition obtained or obtainable by the process of the second aspect.

Preferably the level of EPA in said enriched or purified fatty acid fatty acid composition is at least 30% by weight of the fatty acids in the composition.

In a sixth aspect the invention provides enriched or purified fatty acid composition of the fourth aspect for use in the treatment of a cardiovascular disorder or obesity related condition.

In a seventh aspect the invention provides a product for human or animal consumption comprising the fatty acid composition of the fourth or fifth aspects.

In a seventh aspect the invention provides use of the microbial biomass according to the first aspect in the production of a high purity EPA composition.

Preferably the high purity EPA composition has at least 60% EPA by weight of total fatty acids.

Preferably the high purity EPA composition has at least 70% EPA by weight of total fatty acids.

Preferably the high purity EPA composition has at least 80% by weight of total fatty acids.

Preferably the high purity EPA composition has at least 90% by weight of total fatty acids.

Preferably the high purity EPA composition has at least 95% by weight of total fatty acids.

Preferably the high purity EPA composition has at least 97% by weight of total fatty acids.

In an eighth aspect the invention provides a diatom grown heterotrophically comprising eicosapentaenoic acid and arachidonic acid in a ratio of at least 14:1 where eicosapentaenoic acid forms at least 1.5% w/w of the dry weight of the diatom.

Preferably the diatom is *Nitzschia laevis*.

In a ninth aspect the invention provides use of the diatom according to the eighth aspect in the production of a high purity EPA composition.

In a tenth aspect the invention provides a lipid mixture derived from the diatom of the eighth aspect comprising eicosapentaenoic acid and arachidonic acid in a ratio of at least 14:1.

In a eleventh aspect the invention provides a fatty acid mixture derived from the diatom of the eighth aspect comprising eicosapentaenoic acid and arachidonic acid in a ratio of at least 14:1

Preferably EPA forms at least 5% of total fatty acids

In a twelfth aspect the invention provides a method of producing a diatom comprising eicosapentaenoic acid and arachidonic acid in a ratio of at least 14:1 and at least 1.5% w/w of the dry cell weight as eicosapentaenoic acid comprising:

a. cultivating diatoms in heterotrophic culture containing a nutrient solution comprising:
   (i) an organic carbon source at an initial concentration of at least 0.5 M carbon
   (ii) a molar ratio of organic carbon to nitrogen of no higher than 30:1 (mol C:mol N) and;
   (iii) a non-limiting source of bioavailable silicon;
b. recovering the diatom from the heterotrophic culture.

Preferably the diatoms are cultivated in heterotrophic culture in a fermenter.

Preferably the cultivation comprises continuous fermentation.

Preferably the diatoms comprise *Nitzschia* species.

Preferably the cultivation is carried out at a temperature of from about 12° C. to about 35° C.

Preferably the cultivation is carried out at a pH of from about 7.0 to about 8.7.

Preferably said carbon source comprises glucose.

Preferably said carbon source is selected from glucose, hydrolysed starch or hydrolysed whey.

Preferably said nitrogen source is in the form of sodium nitrate or potassium nitrate.

Preferably a said nitrogen source is supplemented with an amino-acid source.

Preferably said amino-acid source is selected from corn-steep liquor, yeast extract, tryptone, peptones, lysine and glutamate.

Preferably the source of bioavailable silicon is in the form of silicate.

Preferably the concentration of silicate does not fall below 150 µM.

Preferably said silicate is in the form of sodium or potassium metasilicate.

Preferably the nutrient solution comprises phosphorous in the form of phosphate.

Preferably the molar ratio of organic carbon to phosphorus in the form of phosphate is no higher than 1250:1 (mol C:mol P).

In a thirteenth aspect the invention provides use of the diatom produced by the method of the twelfth aspect in the production of a high purity EPA composition.

In a fourteenth aspect the invention provides a process for producing lipid material containing EPA comprising:

a. cultivating diatoms in a fermenter containing a nutrient solution having a molar ratio of available carbon to nitrogen of from 1:1 to 30:1, and a source of bioavailable silicon;
b. maintaining the temperature of said nutrient solution at from about 12° C. to about 35° C. and maintaining the pH of said nutrient solution at from about pH7.0 to about pH8.7;

c. harvesting diatoms from the fermenter; and
d. recovering lipid material containing EPA from the harvested diatoms.

Preferably fresh nutrient solution having a molar ratio of available carbon to nitrogen of from 1 to 30 is added to the fermenter during the course of the cultivation.

Preferably diatoms are harvested from the fermenter at such a rate as the average number of diatoms in the fermenter remains constant over time when the harvested volume is replaced with fresh nutrient solution having a molar ratio of available carbon to nitrogen of from 1 to 30.

Preferably the source of bioavailable silicon is in the form of silicate.

Preferably silicate is added to the fermenter such that the concentration of silicate does not fall below 150 µM.

Preferably the molar ratio of carbon to silicon in the form of silicate source is of from 100:1 to 850:1.

Preferably the nutrient solution comprises phosphorous in the form of phosphate.

Preferably the molar ratio of carbon to phosphorus in the form of phosphate is from 100:1 to 1250:1.

In a fifteenth aspect the invention provides a method of producing a diatom containing eicosapentaenoic acid and arachidonic acid in a ratio of at least 14:1 and in which eicosapentaenoic acid forms at least 1.5% of dry cell weight comprising cultivating heterotrophic diatoms under conditions designed to induce permanent phenotypic change and screening the resultant population of diatoms for isolates in which the ratio of eicosapentaenoic acid and arachidonic acid is at least 14:1.

Preferably the conditions include a mutagenic agent.

Preferably the conditions include an agent selective for increased EPA productivity.

Preferably the conditions include an agent selective for decreased ARA productivity.

BRIEF DESCRIPTION OF THE DRAWINGS

Embodiments of the invention will now be described, by way of example only, with reference to the accompanying drawings in which:

FIG. 1: Shows the relationship between EPA:ARA ratios in biomass and minimum sodium metasilicate concentrations in the medium within which the biomass is formed.

DETAILED DESCRIPTION OF THE INVENTION

Unexpectedly the present inventors have found that it is possible to obtain compositions from heterotrophic microorganisms comprising EPA which contain a ratio of EPA to ARA of around 11:1 or more whilst at the same time also containing EPA at more than 8 fold the level of all co-concentrating fatty acids combined. Such microorganisms are able to be produced in culture at a yield rate in excess of 5 mg EPA/L/hr and with an EPA content greater than 1.5% of total dry cell weight making them relevant in an industrial process.

Also unexpectedly the inventors have found that it is possible to obtain compositions from heterotrophic diatoms comprising EPA which contain a ratio of EPA to ARA of around 14:1 or more. Such microorganisms are able to be produced in culture at a yield rate in excess of 5 mg EPA/L/hr and with an EPA content greater than 1.5% of total dry cell weight making them relevant in an industrial process.

A part of the present invention is the recognition that it is not only desirable, for the purpose of concentrating the fatty acid mixture, to control the amounts of co-concentrating fatty acids (as defined herein) relative to EPA which are allowed to accumulate in the heterotrophic culture of microorganisms, but that it is also feasible to do so through controlling the growth conditions of these microorganisms.

Another part of the present invention is the recognition that it is not only desirable to control the relative amounts of physiochemically or structurally similar molecules to EPA which are allowed to accumulate in the heterotrophic culture of microorganisms for the purposes of EPA purification but that it is also feasible to do so through controlling the growth conditions of these microorganisms.

A further part of the present invention is the recognition that it is the relative rather than absolute levels of molecules that are physiochemically and structurally similar to EPA that are critical to concentration and purification and that, surprisingly, maximal production of EPA in biomass does not necessarily equate to maximal production of highly purified EPA.

Accordingly, the invention provides a microbial biomass produced from a heterotrophic fermentation whose fatty acid profile exhibits:
  an eicosapentanoic acid (EPA) to arachidonic acid (ARA) ratio of about 11:1 or more; and
  an EPA to total co-concentrating fatty acid ratio of about 8:1 or more
The invention further provides:
  a diatom grown heterotrophically comprising eicosapentanoic acid and arachidonic acid in a ratio of at least 14:1 where eicosapentaenoic acid forms at least 1.5% of the dry weight of the diatom;
  a method of producing a diatom comprising an eicosapentaenoic acid to arachidonic acid ratio of at least 14:1 and at least 1.5% of dry cell weight as eicosapentaenoic acid comprising:
    a. cultivating diatoms in heterotrophic culture containing a nutrient solution characterized in that it comprises:
      (i) an organic carbon source at an initial concentration of at least 0.5 M carbon;
      (ii) a molar ratio of organic carbon to nitrogen of no higher than 30:1 (mol C:mol N);
      (iii) a non-limiting source of bioavailable silicon;
    b. recovering the diatom from the heterotrophic culture.

DEFINITIONS AND ABBREVIATIONS

Omega-3 fatty acid is a fatty acid with the first double bond three carbon atoms from the n-methyl end of the molecule. Omega-3 is often shortened to n-3.

Omega-6 fatty acid is a fatty acid with the first double bond six carbon atoms from the n-methyl end of the molecule. Omega-6 is often shortened to n-6.

Fatty acids are described in the form CX:Y, wherein the number X describes the number of carbon atoms and the number Y describes the number of double bonds in the fatty acid. Where Y equals zero the fatty acid is described as saturated, where Y is greater than zero the fatty acid is described as unsaturated. The position and type of the double bonds may be specified as, for example, "cis 5, 11, 14" where the numbers reflect the location of the carbon-carbon double bonds, counting from the carboxylic acid end of the molecule.

A term such as C20:5 is understood to include both the free fatty acid and esterified forms of the fatty acid with the number of carbon atoms and double bonds referring solely to the fatty acid portion of the ester.

EPA, C20:5 n-3, Eicosapentaenoic acid, is an omega-3 fatty acid with twenty carbon atoms and five double bonds.

ARA, C20:4 n-6, Arachidonic acid, is an omega-6 fatty acid with twenty carbon atoms and four double bonds.

Co-concentrating fatty acids are defined as fatty acids, excluding EPA and ARA, that comprise 20 carbons or more and contain at least one double bond. These include but are not limited to the various forms of C20:1, C20:2, C20:3, C20:4, C22:5, C22:6, and C24:1.

DHA, C22:6 n-3, Docosahexanoic acid, is an omega-3 fatty acid with twenty-two carbon atoms and six double bonds.

DPA, C22:5 n-3, Docosapentaenoic acid, is an omega-3 fatty acid with twenty-two carbon atoms and five double bonds.

DGLA, C20:3 n-6, Dihomo-gamma-linoleic acid is an omega-6 fatty acid with twenty carbon atoms with three double bonds.

ETAn-3, C20:4n-3, Eicosatetraenoic acid is an omega-3 fatty acid with twenty carbon atoms and four double bonds.

TFA, Total Fatty Acids means the sum of all fatty acids in a composition or mixture.

DCW, dry cell weight means the weight of a biomass once all water has been removed.

Heterotrophic culture means a culture of organisms for which at least 90% of the energy supply for the culture is derived from supplied nutrients which are usually a form or forms of organic carbon (e.g. glucose, acetate). Therefore a maximum of 10% of the energy supply is derived from light energy. Preferably, less than 5% or less than 1% of the energy supply is derived from light energy. More preferably, the whole of the energy supply is from supplied nutrients.

Photoautotrophic culture means a culture of organisms for which the sole energy source is light.

Mixotrophic culture means a culture of organisms for which the energy source is a mixture of 10% or greater light energy and less than 90% derivatives of supplied nutrients.

Nutrient limitation means that the absence or low level of the nutrient in question causes the organism to grow more slowly than it would if the nutrient were present at higher levels. Non-limiting nutrient provision therefore means that factors other than the nutrient in question are limiting on the growth of the organism and provision of higher amounts of the nutrient in question would not have a the effect of increasing growth. The nutrient is therefore present in sufficient quantities that it does not become exhausted by its incorporation into the biomass such that the free concentration in the nutrient solution does not fall to zero.

COMPOSITIONS OF THE INVENTION

Genetically engineered microorganisms are potentially able to accumulate significant levels of EPA when produced in heterotrophic culture. Damude et al. in US20060115881 provide compositions comprising EPA produced in strains of genetically engineered yeasts. These however contain relatively low ratios of EPA to other molecules which are physiochemically and structurally similar to EPA rendering them poorly suited to concentration and purification. The authors do not teach anything about the relevance of co-concentrating fatty acids to the production of purified EPA and do not suggest how this problem might be addressed.

Xue et al. in US2009/0093543 provide compositions comprising EPA produced in strains of genetically engineered yeasts. One of these compositions is now available commercially and currently marketed as Futurebiotics Newharvest OMEGA-3. The compositions described contain particularly high amounts of EPA (over 50% of total fatty acids in some cases) and low amounts of ARA but contain significant amounts of co-concentrating C20 fatty acids rendering them poorly suited to the present purpose. In addition, the authors disclose the presence of juniperonic acid (C20:4 cis 5, 11, 14, 17) in the fatty acid profile of at least one of their genetically engineered yeast strains. This fatty acid is not only physiochemically and structurally similar to EPA making it particularly difficult to separate but is also not normally found in the human diet, rendering it particularly problematic as a contaminant in any purified EPA product for use in humans. The authors do not teach the relevance of reducing the proportions of co-contaminating fatty acids to the production of purified EPA or how such compositions could be achieved.

In U.S. Pat. No. 5,683,898 & U.S. Pat. No. 5,798,259, Yazawa et al. provide transgenic *E. coli* cultures with EPA around 1.5% of total fatty acids. The authors do not specify the presence or absence of other fatty acids in their material and do not discuss purification of EPA from their material. The authors do not teach anything about the relevance of co-concentrating fatty acids to the production of purified EPA and do not suggest how this problem might be addressed.

Neither Damude et al., Xue et al., Yazawa et al. or any other authors have provided compositions comprising EPA produced in transgenic microorganisms that at the same time contain sufficiently high ratios of EPA to other physiochemically or structurally similar fatty acids to make them suitable for concentration and purification.

Furthermore neither Damude et al., Xue et al., Yazawa et al. nor any other authors have taught that cultured microorganisms should comprise prescribed ranges for ratios of EPA to other physiochemically or structurally similar molecules as taught herein, nor do they teach specifically how the elimination of such molecules is to be achieved.

Certain prokaryotic microorganisms, including but not limited to certain strains of non-genetically engineered (non-GE) marine bacteria have an inherent capacity to produce EPA de novo and are able to accumulate quantities of EPA in culture without recourse to genetic modification. For example, Yazawa et al. (*J. Biochem.* 103: 5-7 1988) provide compositions comprising EPA from the non-GE SCRC-8132 bacterium. The authors state that "Rather surprisingly, other polyunsaturated fatty acids, such as arachidonic (C20:4) . . . were not detected at all [in the cultured bacterium]" and "this unique fatty acid composition makes it easy to isolate EPA from a culture of this bacterial strain" but do not comment on other C20 fatty acids and their role in concentration. In addition, the authors do not teach how high levels of EPA and low levels of ARA might be achieved in culture of a eukaryotic organism. Bowman et al. (*Int J Syst Bacteriol* 47: 1040-1047, 1997) provide compositions comprising prokaryotic microorganisms with high levels of EPA as a proportion of total fatty acids. The authors do not record C20 fatty acids other than EPA and ARA, and in some cases appear not to have measured ARA thus do not disclose our composition. Neither do the authors teach the relevance of such compositions to concentration and purification or suggest how such compositions might be obtained in culture of a eukaryotic organism.

None of these prokaryotic sources have been able to be commercialized due to low levels of yield. The maximum yield rate reported by Yazawa et al. for example is 1.1 mg EPA/L/hr but with EPA forming less than 0.5% of the dry cell weight. Non-GE prokaryotes cannot compete as a source of EPA with eukaryotic microorganisms due to the relatively low dry weight of EPA and are therefore poorly suited to the present purpose. Since prokaryotic and eukaryotic organisms are fundamentally different, teachings from one cannot be directly applied to the other so there can be no reasonable expectation that the observations of Yazawa et al., or Bowman et al. nor of any other author on the EPA content of naturally occurring prokaryotic organisms could be used to further develop eukaryotic EPA production.

A number of authors provide compositions comprising EPA as a component of a microorganism produced in cultures of naturally occurring eukaryotic microorganisms utilising light as their main energy source for growth. If light is the sole energy source these cultures are deemed photosynthetic or photoautotrophic. Organic carbon may be added to a photosynthetic culture to render it mixotrophic. These cultures are generally produced in ponds or open raceways, or in photobioreactors supplied internally with large amounts of artificial light and/or comprised of transparent material with high surface to volume ratios to allow light to pass into the culture. The low yields, high capital costs and/or technical difficulties associated with such production and the consequent costs of producing EPA in this way render them unsuitable for the present purpose.

For example, Vazhappilly and Chen (*JAOCS* 75: 393-397, 1998) provide compositions comprising EPA in a number of species of microalgae grown under photoautotrophic conditions and the best of these only showed average growth rates of around 256 mg cells per day with many showing far lower. The authors note that "The high accumulation of arachidonic acid (ARA, C20:4n-6) with EPA or DHA is disadvantageous because ARA can case deleterious health effects and problems in EPA recovery" but do not suggest means of reducing ARA content in heterotrophic culture. In addition the authors state "The ARA culture was relatively low in all 20 microalgae except in *Por[phyridium] cruentum*". Since many of the species mentioned have very similar amounts of the two fatty acids and two even have more ARA than EPA, this suggests that the authors consider the absolute amount of ARA is important rather than the ratio of EPA to ARA. This teaches away from our invention as we teach that it is the ratio of EPA to ARA that is important rather than the absolute amount of either fatty acid.

Certain non-GE eukaryotic microorganisms, including but not limited to certain microalgae, fungi and yeasts, are capable of being grown heterotrophically and are able to accumulate significant levels of EPA when produced in heterotrophic culture. These have the advantages that they can be produced indoors in conventional steam sterilisable reactors with relatively low surface to volume ratios as compared to photobioreactors.

Yongmanitchai and Ward (*Process Biochemistry* 24: 117-125, 1989) provide a list of microorganisms that produce EPA and DHA. The authors do not distinguish between organisms that can be grown heterotrophically or must be grown photosynthetically so it is impossible to anticipate from this reference whether these organisms are suitable for industrial production of EPA. Neither is it possible to determine if the fatty acid compositional data disclosed are from cultures grown heterotrophically. In no cases do the data provided on the fatty acid content of the organisms allow full identification of the content of EPA relative to ARA and other co-concentrating fatty acids such that they describe the composition of this invention. The authors discuss the production of high purity EPA but do not discuss the effect that other polyunsaturated fatty acids have on the ease with which EPA may be purified. The reference neither suggests the composition described herein, that such a composition is relevant to concentration and purification, nor that there is any expectation that one could be successful in obtaining such a composition.

Barclay in U.S. Pat. No. 5,130,242 and U.S. Pat. No. 5,908,622 reports the isolation, heterotrophic growth and fatty acid profiles of a number of algal strains. The simultaneous presence of EPA and absence of ARA is reported for a number of these (grown under standard screening conditions), whilst a number more have low levels of ARA as compared to EPA. The majority of these have ratios of EPA:DHA lower than 8 rendering them poorly suited for the present purposes.

Strain BRBG is reported in table 3 of U.S. Pat. No. 5,130,242 as having no AA (ARA) and a ratio of EPA to DHA of 12 and in table 4 as having an EPA to DHA ratio of 10.9. The same data is used in U.S. Pat. No. 5,908,622.

Dihomo-gamma-linoleic acid (DGLA) or eicosatetraenoic acid (ETA) are, however, not reported so the author clearly does not recognise the importance of the relative levels other long chain fatty acids of 20 carbons or more for the purposes of concentration and purification. Given the relatively low amounts of EPA in the fatty acid profile, even small amounts of these or other C20 compounds could have a significant effect on the ratio of EPA to co-concentrating fatty acids. No productivity data is provided for the growth of these strains.

The author considers purification of omega-3 fatty acids as a group but does not consider purification of individual fatty acids thus does not teach the relevance of composition to concentration and purification of individual fatty acids.

Whilst noting that omega-6 fatty acids including ARA are disadvantageous for dietary purposes, the author states that "strains can also be isolated which have less than 1% (as % total fatty acids) of the undesirable C20:4n-6 and C22:5n-6 HUFAs for some applications" indicating that this author considers the total amount rather than the relative amount of ARA to be important. This teaches away from the present invention which teaches that it is the ratio of EPA to ARA that is important rather than the absolute amount of either fatty acid.

A number of authors provide compositions comprising EPA produced in diatoms. For example, Tan and Johns (*Journal of Applied Phycology* 8: 59-64, 1996) report heterotrophic growth of several diatoms but neither record nor mention ARA content of the cells or content of other co-concentrating fatty acids other than C20:3. The reference neither suggests the composition described herein, that such a composition is relevant to concentration and purification, nor that there is any expectation that one could be successful in obtaining such a composition.

Kitano et al. (*Journal of Applied Phycology* 9: 559-563, 1997) report heterotrophic growth of the diatom *Navicula saprophila* but the ratio of EPA to C20:4 obtained is less than 10. The content of other long chain fatty acids of 20 carbons or more is not disclosed nor is any consideration given to purification. The reference neither suggests our composition, that such a composition is relevant to concentration and purification, nor that there is any expectation that one could be successful in obtaining such a composition.

In U.S. Pat. No. 5,244,921 and 5567732 Kyle and Gladue disclose methods of producing Eicosapentaenoic acid from the diatom *Nitzschia alba* in heterotrophic culture. In cells produced by their methods the ratio of EPA to C20:4 is only 4:1. The ratio of EPA to other co-concentrating fatty acids is not considered nor is the likely effect on purification. The reference neither suggests our composition, that such a composition is relevant to concentration and purification, nor that there is any expectation that one could be successful in obtaining such a composition.

Chu et al. (*Journal of Applied Phycology* 8: 389-396, 1996) report heterotrophic culture of the diatom *Nitzschia inconspicua* on acetate and glucose. The authors do not disclose the content of long chain fatty acids of 20 carbons or more, other than EPA and ARA. The ratio of these two fatty acids is, in any case, lower than 2 under heterotrophic conditions. The reference neither suggests the composition described herein, that such a composition is relevant to concentration and purification, nor that there is any expectation that one could be successful in obtaining such a composition.

Wen and Chen in a number of papers (*Biotechnology Letters* 22: 727-733, 2000; *Journal of Industrial Microbiology & Biotechnology* 25: 218-224, 2000; *Enzyme and Microbial Technology* 29: 341-347, 2001; *Biotechnol Bioeng* 75: 159-169, 2001; *Biotechnol. Prog.* 18: 21-28, 2002; *Process Biochemistry* 37:1447-1453, 2002; *Process Biochemistry* 38: 523-529, 2002) have described optimisation of heterotrophic growth conditions for the diatom *Nitzschia laevis*. The authors work to maximise the production of EPA but have given no indication that the ratio of EPA to ARA is important or that optimising the ratio is considered. Likewise there is no consideration of the relative levels of EPA to co-concentrating fatty acids, or of concentration or purification. The references neither teach the composition described herein, nor suggest that this composition is relevant to concentration and purification.

In Pahl et al. (*J Bioscience and Bioeng* 109: 235-239, 2010) the authors report heterotrophic growth of the diatom *Cyclotella cryptica* for the purposes of producing feed for use in the aquaculture industry. The authors do not consider the possibility of producing purified EPA nor the effect that the relative levels of EPA to other long chain fatty acids would have on concentration or purification. In particular, the amounts of ARA are not even reported in the paper. The authors use a media rich in nitrogen sources, phosphates and silicate but with relatively low amounts of carbon. As a result, the EPA content of the cells remains below 1.5% of dry cell weight. The reference neither suggests the composition described herein, that such a composition is relevant to concentration and purification, nor that there is any expectation that one could be successful in obtaining such a composition.

Griffiths and Geiringer in WO2008004900 provide compositions comprising EPA with low levels of molecules with structural and physiochemical properties similar to EPA derived from diatoms. These authors disclose the general desirability of compositions comprising EPA with low levels of certain fatty acids for pharmacotherapeutic use. In particular ARA and other omega-3 and omega-6 fatty acids which "may diminish the desired effect through actions which may be antagonistic, competitive, block, reverse, mediate, synergise or otherwise alter the desired beneficial health effect of EPA" are classed as undesired. The authors also disclose the general desirability of compositions comprising EPA with low levels of the aforementioned undesired fatty acids for the purposes of purification for later pharmacotherapeutic use. They do not consider other C20 fatty acids that have no effect on the beneficial health effect of EPA but that would affect the degree to which it may be concentrated or purified.

While the authors teach the desirability of EPA compositions with low levels of ARA for therapeutic purposes, they fail to suggest the compositions of the present invention because their compositions require a first isolation step from biomass, and their compositions do not take into account all co-concentrating fatty acids, merely those which have effects on the biological activity of EPA. Furthermore, there is no teaching on how the compositions of the present invention could be obtained or the industrial use of doing so.

Furthermore, neither Griffiths and Geiringer, nor any other authors have taught that prescribed ranges for ratios of EPA to ARA or co-concentrating fatty acid molecules as taught herein are important in heterotrophic culture of microorganisms such that they result in a composition amenable to a high degree of concentration and then purification.

Whilst heterotrophic cultures of microorganisms, and in particular naturally occurring eukaryotic microalgae may be able to act as an alternate omega-3 fatty acid source to fish through accumulation of large quantities of EPA in culture, it may seem surprising that relatively little if any systematic effort has been devoted to the development of such sources of EPA which are at the same time sufficiently free of physiochemically or structurally similar molecules to EPA to allow a high degree of concentration and purification.

In a first broad aspect the invention provides a composition comprising heterotrophically-grown microorganisms in which the ratio of EPA to ARA is at least 11:1 and the ratio of EPA to co-concentrating fatty acids is at least 8:1, where the ratios are on a weight to weight basis.

Preferably the composition comprises a ratio of EPA to ARA of at least 12:1, more preferably the ratio is at least 13:1, more preferably at least 14:1, and even more preferably at least 15:1.

Preferably the composition comprises a ratio of EPA to co-concentrating fatty acids of at least 9:1, more preferably the ratio is at least 10:1, more preferably at least 11:1 and even more preferably at least 12:1.

Preferably, less than 1% w/w of the total fatty acids is juniperonic acid (being a co-concentrating fatty acid). More preferably the composition comprises less than 0.5% w/w juniperonic acid. Most preferably no juniperonic acid is present in the composition.

Preferably, less than 1% w/w of the total fatty acids is sciadonic acid (being a co-concentrating fatty acid). More preferably the composition comprises less than 0.5% w/w sciadonic acid. Most preferably no sciadonic acid is present in the composition.

Preferably the heterotrophically grown micro-organisms are eukaryotic. Typically, the micro-organisms comprise identified microalgae, or fungi. Preferably the micro-organisms are comprised of microalgae. More preferably the micro-organisms are comprised of diatoms, preferably marine diatoms, more preferably the micro-organisms are comprised of marine single-celled diatoms from the genus *Nitzschia*, even more preferably the micro-organisms are comprised of the marine single-celled diatom known as *Nitzschia laevis*.

Preferably the strain of micro-organism selected, when under culture conditions, for an improved yield of recoverable EPA. The micro-organism preferably comprises a strain of micro-organism selected, when under culture conditions, for a decreased yield of recoverable ARA relative to EPA. The micro-organism preferably comprises a strain of micro-organism selected, when under culture conditions, for a decreased yield of recoverable co-concentrating fatty acids relative to EPA.

In one aspect, the composition described above is a microbial biomass.

Preferably the biomass composition comprises a proportion of its total dry weight as fatty acids; the proportion lying in the range of between 5 and 80% a proportion of which will be EPA; the proportion of EPA (by dry weights of the fatty acids) lying in the range of between 2 and 80% more preferably the proportion is more than 10%, more preferably over 20% and even more preferably over 30%. Typically, the proportion (by dry weights) of total fatty acids that is EPA is in the range from 10 to 80%, from 20 to 80% or from 30 to 80%.

The invention therefore provides a microbial biomass produced from a heterotrophic fermentation, the biomass having a fatty acid profile exhibiting:

an eicosapentaenoic acid (EPA) to arachidonic acid (ARA) ratio of about 11:1 or more;

an EPA to total co-concentrating fatty acid ratio of about 8:1 or more.

Preferably, no juniperonic acid (JPA) or sciadonic acid is present in the biomass.

Typically, the microbial biomass is a eukaryotic microbial biomass, most typically a microalgal biomass. Most preferably, the microalgal biomass is marine diatom biomass such as a *Nitzschia laevis* biomass.

Typically the microbial biomass is produced from a microbial culture by harvesting the microbes from the heterotrophic culture medium, optionally heat or otherwise killing the cells (for example to denature endogenous enzymes) and forming the cells into a biomass (e.g. a cake of biomass). The biomass is optionally dried to reduce or eliminate water. Formation of the biomass of the invention does not include extraction or purification steps to recover fatty acids or materials other than water. However, the EPA:ARA ratio of the biomass of the invention serves to facilitate the subsequent extraction and purification steps used to enrich the EPA for therapeutic purposes.

The microbial biomass of the invention may be subjected to one or more extraction steps to extract fatty acids from the biomass to yield a fatty acid composition. Suitable extraction techniques are well known in the art. For example, the biomass may be extracted with a non-selective lipid solvent (e.g near critical di-methyl ether or ethanol) and recovered from the solvent as a residue.

Following extraction, the level of EPA in said fatty acid composition is from 5 to 90%, from 5 to 75% or from 5 to 50% by weight of the fatty acids in the composition. The ratio of EPA to ARA is able to be retained at substantially the same level as prior to extraction, preferably at least 11:1. The ratio of EPA to total co-concentrating fatty acid is able to be retained at substantially the same level as prior to extraction, preferably at least about 8:1.

Following extraction, the further step of enriching the fatty acid composition in EPA or purifying EPA from the fatty acid composition may be performed using techniques well known in the art. For example, the extracted material may be treated with acids, alkalis and/or enzymes in the presence of alcohol or water to form fatty acid or fatty acid alkyl ester mixtures. The mixtures may then be further concentrated and purified in order to achieve a required standard of purity. The ratio of EPA to ARA in the composition is able to be retained at substantially the same level as prior to enriching and/or purifying, preferably at least 11:1. The ratio of EPA to total co-concentrating fatty acid in the composition is also able to be retained at substantially the same level as prior to enriching and/or purifying, preferably at least about 8:1. More preferably, the ratios of EPA to ARA and EPA to total co-concentrating fatty acid will increase following the enriching and/or purifying step. However, given the relative difficulty and cost in separating EPA from ARA and the co-concentrating fatty acids there is an advantage in having relatively high ratios of EPA to ARA and EPA to co-concentrating fatty acids in the composition prior to the enriching and/or purifying step.

Following enrichment or purification, the level of EPA in said fatty acid composition is at least 30%, or at least 50%, or is a high purity EPA composition of at least 60%, at least about 70%, at least 80%, at least 90%, at least 95% or at least 97% by weight of the fatty acids in the composition. High purity EPA composition for the purposes of this specification can be defined accordingly. Such a high purity EPA composition forming another aspect of the invention.

In a related aspect, the invention provides fatty acid and lipid mixtures derived from a composition comprising heterotrophically-grown microorganisms in which the ratio of EPA to ARA is at least 11:1 and the ratio of EPA to co-concentrating fatty acids is at least 8:1.

In a further alternative aspect the invention provides for use of a composition comprising heterotrophically-grown microorganisms in which the ratio of EPA to ARA is at least 11:1 and the ratio of EPA to co-concentrating fatty acids is at least 8:1, in the manufacture of a product for human or animal consumption. Such a product could be formulated by a person skilled in the art using known techniques, and may include, for example, fillers, carriers, buffers, stabilisers and preservatives. It may take the form of, for example, tablets, capsules, liquids, solutions, and may also be combined with other products food products such as breads and cereals, spreads, and dairy products.

In a related aspect, the invention provides for use of a composition comprising heterotrophically-grown microorganisms in which the ratio of EPA to ARA is at least 11:1 and the ratio of EPA to co-concentrating fatty acids is at least 8:1, in the manufacture of a product comprising the composition blended with other fatty acids or fatty acid alkyl esters.

In a further alternative aspect the invention provides for use of a composition comprising heterotrophically-grown microorganisms in which the ratio of EPA to ARA is at least 11:1 and the ratio of EPA to co-concentrating fatty acids is at least 8:1, in the manufacture of a medicament for treatment of a person affected by certain medical conditions or disorders including but not limited to those selected from diabetes (type I, and type II), glycaemic disorders diabetes-associated hypertension, cancer, osteoarthritis, autoimmune diseases, rheumatoid arthritis, inflammatory and auto-immune diseases other than arthritis, respiratory diseases, neurological disorders, neurodegenerative disorders (including Huntington's disease, Parkinson's disease, Alzheimer's disease, schizophrenia, major depression, unipolar depression, bipolar depression, obsessive compulsive disorder, borderline personality disorder, post natal depression, organic brain damage, and traumatic brain injury), renal and urinary tract disorders, cardiovascular disorders, cerebrovascular disorders, degenerative diseases of the eye, psychiatric disorders, reproductive disorders, visceral disorders, muscular disorders, metabolic disorders, prostatic hypertrophy and prostatitis, impotence and male infertility, mastalgia, male pattern baldness, osteoporosis, dermatological disorders, dyslexia and other learning disabilities, cancer cachexia, obesity, ulcerative colitis, Crohn's disease, anorexia nervosa, burns, osteoarthritis, osteoporosis, attention deficit/hyperactivity disorder, and early stages of colorectal cancer, lung and kidney diseases, and disorders associated with abnormal growth and development. Preferably the medical condition of disorder is a cardiovascular disorder or obesity related condition.

In a second broad aspect the invention provides a composition comprising heterotrophically-grown diatoms in which the ratio of EPA to ARA is at least 14:1.

Preferably the composition comprises a ratio of EPA to ARA of at least 15:1, more preferably the ratio is at least 16:1, more preferably at least 17:1 and even more preferably at least 18:1.

Preferably the diatoms are comprised of marine single-celled diatoms from the genus *Nitzschia*. Preferably the diatoms are comprised of the marine single-celled diatom known as *Nitzschia laevis*.

The diatom will comprise a strain of diatom selected, when under culture conditions, for an improved yield of recoverable EPA.

In an alternative aspect, the diatom comprises a strain of diatom selected, when under culture conditions, for a decreased yield of recoverable ARA relative to EPA.

Preferably the diatom composition comprises a proportion of its total dry weight as fatty acids; the proportion lying in the range of between 5 and 80% a proportion of which is EPA; the proportion of EPA of the fatty acids (by dry weights) lying in the range of between 2 and 80% more preferably the proportion is more than 10%, more preferably over 20% and even more preferably over 30%.

In a related aspect, the invention provides lipid and fatty acid mixtures derived a composition comprising heterotrophically-grown diatoms in which the ratio of EPA to ARA is at least 14:1.

In a further alternative aspect the invention provides for use of a composition comprising heterotrophically-grown diatoms in which the ratio of EPA to ARA is at least 14:1, in the manufacture of a product for human or animal consumption.

In a related aspect, the invention provides for use of a composition comprising heterotrophically-grown diatoms in which the ratio of EPA to ARA is at least 14:1, in the manufacture of a product comprising the composition blended with other fatty acids or fatty acid alkyl esters.

In a further alternative aspect the invention provides for use of a composition comprising heterotrophically-grown diatoms in which the ratio of EPA to ARA is at least 14:1, in the manufacture of a medicament for treatment of a person affected by certain medical conditions or disorders including but not limited to those selected from diabetes (type I, and type II), glycaemic disorders diabetes-associated hypertension, cancer, osteoarthritis, autoimmune diseases, rheumatoid arthritis, inflammatory and auto-immune diseases other than arthritis, respiratory diseases, neurological disorders, neurodegenerative disorders (including Huntington's disease, Parkinson's disease, Alzheimer's disease, schizophrenia, major depression, unipolar depression, bipolar depression, obsessive compulsive disorder, borderline personality disorder, post natal depression, organic brain damage, and traumatic brain injury), renal and urinary tract disorders, cardiovascular disorders, cerebrovascular disorders, degenerative diseases of the eye, psychiatric disorders, reproductive disorders, visceral disorders, muscular disorders, metabolic disorders, prostatic hypertrophy and prostatitis, impotence and male infertility, mastalgia, male pattern baldness, osteoporosis, dermatological disorders, dyslexia and other learning disabilities, cancer cachexia, obesity, ulcerative colitis, Crohn's disease, anorexia nervosa, burns, osteoarthritis, osteoporosis, attention deficit/hyperactivity disorder, and early stages of colorectal cancer, lung and kidney diseases, and disorders associated with abnormal growth and development. Preferably the medical condition of disorder is a cardiovascular disorder or obesity related condition. Manufacture of the medicament, will be well know to the skilled person, Such a medicament could be formulated by a person skilled in the art using known techniques, and may include, for example, pharmaceutically acceptable fillers, carriers, buffers, stabilisers and/or preservatives. It may take the form of, for example, tablets, capsules, liquids and/or solutions.

PROCESSES OF THE INVENTION

A number of authors teach methods by which diatoms may be grown to produce EPA. For example, Tan and Johns (*Journal Applied Phycology* 8: 59-64, 1996) report heterotrophic growth of several diatoms but neither record nor mention ARA content of the cells or the content of fatty acids with more than 20 carbon atoms other than C20:3. Other than examining photosynthetic and mixotrophic growth modes, the authors do not attempt any variation in nutrients nor comment on the fact that this could affect fatty acid composition. These authors do not suggest the process of the present invention as they do not recognise that relative ratios of carbon, nitrogen, silicate and phosphate nutrients will have an effect on fatty acid composition. Nor do the authors disclose that affecting the relative ratios of EPA to ARA in biomass through nutrient content of the growth media might be desirable.

Kitano et al. (*Journal of Applied Phycology* 9: 559-563, 1997) report heterotrophic growth of the diatom *Navicula saprophila* but the ratio of EPA to C20:4 obtained is less than 10. Other than examining photosynthetic and mixotrophic growth modes, the authors do not attempt any variation in nutrients nor comment on the fact that this affects fatty acid composition. These authors do not suggest the process of the present invention as they do not recognise that relative ratios of carbon, nitrogen, silicate and phosphate nutrients will have an effect on fatty acid composition. Nor do the authors disclose that affecting the relative ratios of EPA to ARA in biomass through nutrient content of the growth media might be desirable.

In U.S. Pat. No. 5,244,921 and 5567732 Kyle and Gladue disclose methods of producing Eicosapentaenoic acid from the diatom *Nitzschia alba* in heterotrophic culture. In this the authors teach away from the current invention by depriving cells first of nitrogen and then subsequently of silicate prior to harvest. The cells accumulate lipid but the ratio of EPA to C20:4 is only 4:1. The ratio of EPA to other long chain fatty acids of −20 carbons or more is not considered nor is the likely effect on purification.

Wen and Chen in a number of papers (*Biotechnology Letters* 22: 727-733, 2000; *Journal of Industrial Microbiology & Biotechnology* 25: 218-224, 2000; *Enzyme and Microbial Technology* 29: 341-347, 2001; *Biotechnol Bioeng* 75: 159-169, 2001; *Biotechnol. Prog.* 18: 21-28, 2002; *Process Biochemistry* 37:1447-1453, 2002; *Process Biochemistry* 38: 523-529, 2002) have described optimisation of heterotrophic growth conditions for the diatom *Nitzschia laevis*. The authors have manipulated nutrient levels in their feed media to maximise the production of EPA but have not attempted to measure any residual nutrients other than glucose, and thus have not investigated the effects of limitation by lack of nitrogen, phosphate or silicate nutrients in the culture itself. The authors have not achieved prescribed ranges for ratios of nutrient components as taught herein, such that a sufficiently high ratio of EPA to ARA can be obtained.

These authors do not suggest the process of the present invention as they do not recognise that limitation by lack of nitrogen or silicate nutrients have an effect on the relative ratios of EPA to ARA in biomass. Nor do the authors disclose that affecting the relative ratios of EPA to ARA in biomass through nutrient content of the growth media might be desirable.

In Pahl et al. (*J Bioscience and Bioeng* 109: 235-239, 2010) the authors report heterotrophic growth of the diatom *Cyclotella cryptica* for the purposes of producing feed for use in the aquaculture industry. The authors use a media rich in nitrogen sources, phosphates and silicate but with relatively low amounts of carbon such that it does not achieved the prescribed nutrient composition as taught herein. The authors do not consider the possibility of producing purified EPA nor the effect that the relative levels of EPA to ARA would have on concentration or purification; the amounts of ARA are not even reported in the paper. The authors note that silicate limitation might be expected to increase the proportion of fatty acids with a lower degree of unsaturation but do not consider that changing nutrient ratios in media might affect the ratio between different highly-unsaturated long chain-fatty acids. These authors do not suggest the process of the present invention as they do not recognise that relative ratios of carbon, nitrogen, silicate and phosphate nutrients will have an effect on the relative ratios of EPA to ARA in biomass. Nor do the authors disclose that affecting the relative ratios of EPA to ARA in biomass through nutrient content of the growth media might be desirable.

Roessler (*J Phycol* 24: 394-400, 1988) examines the effects of silicon deficiency in photoautotrophic cultures of the diatom *Cyclotella cryptica*. The author notes that silicon deficiency increases the amount of lipid in the cell matter but decreases the relative proportion of PUFAs and even suggests that if biomass is being produced for production of PUFAs that the growth medium should be nutrient replete. The author does not, however, comment on any change in ratio between the PUFAs that silicate deficiency causes. Furthermore, there is no consideration of concentration or purification of EPA from the material and the importance of the relative levels of EPA to other long chain fatty acids of 20 carbons or more for this purpose. The author does not suggest the process of the present invention as their process uses light as the primary source of energy for the culture. Nor do they suggest success in processes which do not use light at the primary source of energy since there is no recognition that relative ratios of carbon, nitrogen, silicate and phosphate nutrients will have an effect on the relative ratios of EPA to ARA in biomass. Nor does the author disclose that affecting the relative ratios of EPA to ARA in biomass through nutrient content of the growth media might be desirable.

Taguchi et al. (*J Phycol* 23: 260-267, 1987) examine lipid content of marine diatoms under conditions of silicate deficiency under photoautotrophic conditions. The authors state "It is essential to establish a critical N:P:Si ratio so that algae can be ensured to utilize silicate at first compared to nitrate and phosphate. Remaining low concentration of nitrate and phosphate keep algae alive to produce more lipid per cell even when algae cannot grow further due to silicate exhaustion from medium" thus indicating that they believe silicate deprivation to be beneficial and teaching away from this invention. The authors do not disclose or consider the fatty acid composition of the cells. The authors do not suggest the process of the present invention as their process uses light as the primary source of energy for the culture. Nor do they suggest success in processes which do not use light at the primary source of energy since the authors teach away from the current invention by depriving cells of silicate to increase lipid yield.

Chu et al. (*Journal of Applied Phycology* 8: 389-396, 1996) report heterotrophic culture of the diatom *Nitzschia inconspicua* on acetate and glucose and also examine the effects of changing levels of available silicon and nitrogen in photosynthetic culture. The authors do not comment on the effect that these changes have on the ratio between EPA and ARA nor is there any consideration of concentration or purification of EPA from the material and the importance of the relative levels of EPA to other long chain fatty acids of 20 carbons or more for this purpose. Furthermore the authors also state "Nitrogen starvation enhanced total fatty acid content of *N. inconspicua*, and highest yield of 20:5 (n-3) was produced when grown at low $NaNO_3$ level." Indicating, contrary to the current invention, that they believe EPA yield to be the most important factor in determining growth conditions. The authors do not suggest the process of the present invention as most of their processes use light as the primary source of energy for the culture. Nor do they suggest success in processes which do not use light at the primary source of energy since the authors teach away from the current invention by depriving cells of nitrogen to increase lipid yield.

Barclay in U.S. Pat. No. 5,130,242 and U.S. Pat. No. 5,908,622 reports the isolation, heterotrophic growth and fatty acid profiles of a number of algal (non-diatom) strains. The author teaches that "If a product significantly higher in lipids and omega-3 highly unsaturated fatty acids is desired, the culture can be manipulated to become nutrient limited, preferably, nitrogen limited for a suitable time . . . " thus teaching directly away from the invention. In addition, the author considers purification of omega-3 fatty acids as a group but does not consider purification of individual fatty acids. Whilst noting that omega-6 fatty acids including ARA are disadvantageous for dietary purposes, the author states that "strains can also be isolated which have less than 1% (as % total fatty acids) of the undesirable C20:4n-6 and C22:5n-6 HUFAs for some applications" indicating that this author considers the total amount rather than the relative amount of ARA to be important contrary to the current invention. The author does not suggest the process of the present invention as the process uses a non-diatom algal culture. Nor do they suggest success in cultures of diatoms since the author teaches away from the current invention by depriving cells of nutrients to increase lipid yield.

No other authors have provided methods by which EPA in heterotrophically grown diatoms can be obtained at a sufficiently high ratio of EPA to ARA to make it amenable to concentration and purification.

Furthermore no other authors have taught that methods to produce cultured diatoms should comprise avoiding nitrogen limitation and maintaining a minimum silicate concentration in culture, preferably through using the prescribed ranges for ratios of nutrient components as taught herein, such that a sufficiently high ratio of EPA to ARA can be obtained.

Whilst processes involving heterotrophic culture of microorganisms, and in particular naturally occurring eukaryotic diatoms may be able to provide an alternate omega-3 fatty acid source to fish through accumulation of large quantities of EPA in culture, it may seem surprising that relatively little if any systematic effort has been devoted to the development of such sources of EPA which are at the same time sufficiently free of physiochemically or structurally similar molecules to EPA to allow a high degree of concentration and purification. Indeed, current methodology stresses the maximisation of the absolute amount of EPA and in doing so frequently disproportionally increases the absolute amount of physiochemically or structurally similar molecules and thereby makes it harder to purify EPA.

Thus, in a third broad aspect the invention provides a process for obtaining the compositions as previously described above wherein the process employs a culture of micro-organisms of a type selected for a capability of heterotrophic growth, and a capability of production of EPA, and a relatively low content of physiochemically or structurally similar molecules to EPA; the process including a culture phase in which cells are grown under conditions in which organic carbon is used as an energy source; the conditions preferably including non-limitation of nutrients selected from a range including phosphorus, nitrogen and/or silicon; said procedures being undertaken in order to maximise the amount of recoverable biomass in which the ratio of EPA to ARA is at least 11:1 (preferably 14:1) and the ratio of EPA to all co-concentrating fatty acids is at least 8:1.

However, the inventors have found that while non-limiting levels of phosphate are preferred, the level of phosphate concentration has less effect on the ratio of EPA to ARA and EPA to co-concentrating fatty acids in comparison to the effect of the levels of nitrogen and/or silicate. Non-limiting levels (or greater excesses) of nutrients are very much preferred as this can have the effect of substantially increasing the EPA:ARA ratio in the final product (refer, FIG. 1, for example).

Different modes of culturing or fermentation are possible. The simplest of which is batch fermentation in which cells are inoculated in nutrient media, grown for a period of time and then harvested. Fed-batch fermentation is similar to batch but differs in that concentrated nutrients are supplied to the culture during the growth period. Continuous fermentation involves the continuous harvest of culture comprising biomass and nutrient solution from the fermentation vessel and its replacement with fresh nutrient solution. The rate of harvest in continuous fermentation is chosen so that the density of the cells in culture remains constant. Semi-continuous fermentation is similar to continuous fermentation except that harvests are periodic rather than continuous. Continuous fermentation or semi-continuous fermentation are preferred for the production of the microbial biomass of the invention but batch or fed-batch fermentation could also be used.

For industrial production of EPA yield rates are important to provide a cost effective process. Higher production rates are preferred for this reason. While production rates below 5 mg EPA/L/hr may still be useful, the inventors have shown production rates of greater than 5 mg EPA/L/hr can be achieved using the methods and processes of the invention where a continuous or semi-continuous fermentation/culture techniques are employed. In a preferred option at least 5 mg EPA is produced per liter of culture per hour. In a more preferred option at least 10 mg EPA is produced per liter of culture per hour.

In addition to yield rates, the level of the EPA (w/w) within the biomass is also important to the industrial applicability of the processes and methods of the invention. In a preferred option EPA forms at least 1.5% of the dry cell weight of the biomass. In a more preferred option EPA forms at least 2% of the dry cell weight of the biomass, in an even more preferred option EPA forms at least 3% of the dry cell weight of the biomass.

In a related aspect the invention provides a process as previously described in this section wherein the culture of micro-organisms comprises identified microalgae, or fungi. Preferably the micro-organisms are comprised of microalgae. More preferably the micro-organisms are comprised of diatoms, preferably marine diatoms, more preferably the micro-organisms are comprised of marine single-celled diatoms from the genus *Nitzschia*, even more preferably the micro-organisms are comprised of the marine single-celled diatom known as *Nitzschia laevis*.

In a related aspect the invention provides a process for producing lipid mixtures and fatty acid mixtures derived from a culture as previously described in this section, wherein the mixtures are obtained by a harvesting process including the steps of:
  harvesting cells from the culture medium;
  optionally, heat or otherwise killing the cells to denature endogenous enzymes; forming the cells into a cake of biomass;
  optionally drying the biomass to reduce or eliminate water;
  extracting the cake of biomass with a non-selective lipid solvent and recovering the extracted material from the solvent as a residue; (for example, use of near critical di-methyl ether is one option, use of ethanol is another)
  optionally treating the extracted material with acids, alkalis and/or enzymes in the presence of an alcohol or water to form fatty acid or fatty acid alkyl ester mixtures and optionally further concentrating and purifying said mixtures in order to achieve a required standard of purity.

Biomass may be harvested or recovered from the culture according to many methods that will be known to persons skilled in the art. These include centrifugation, filtration, settling and decantation. Alternatively the whole culture can be collected and subjected to drying or lipid extraction procedures.

In a fourth broad aspect the invention provides a process for culturing diatoms wherein the process employs a culture of diatoms selected for a capability of heterotrophic growth and a capability of production of EPA, and a relatively low content of physiochemically or structurally similar molecules to EPA; the process including a culture phase in which cells are grown in a nutrient solution comprising:
  an organic carbon source at an initial concentration of at least 0.5 M carbon;
  one or more nitrogen sources at an initial concentration sufficiently high to ensure that nitrogen limitation does not occur (a molar ratio of organic carbon to nitrogen of no higher than 30 (mol C:mol N) is preferred);
  a concentration of bioavailable silicon in sufficient quantities that silicon limitation does not occur (preferably the bioavailable silicon is in the form of silicate and preferably the concentration of silicate does not fall below 150 µM).

In a preferred aspect, the initial concentration of organic carbon source is from 0.5 M to 10 M, from 1 M to 10 M, or from 5 M to 10 M.

In a preferred aspect, the ratio of organic carbon to nitrogen is from 1 to 30, from 5 to 30, from 10 to 30, or from 15 to 30.

In a preferred aspect the molar ratio of organic carbon to phosphorus in the form of phosphate of no higher than 1250 (mol C:mol P), in a more preferred aspect the molar ratio is no higher than 750. Typically, the molar ratio is from 100 to 1250, from 250 to 1250, from 250 to 750 or from 350 to 650 (mol C: mol P).

Bioavailable silicon means a compound of silicon that can be taken up and incorporated into biomass. This may take the form of silicic acid or an alkali metal silicate. Preferably sodium metasilicate or potassium metasilicate is used.

In a preferred aspect the concentration of silicon in the form of silicate is no lower 150 µM at any time during the culture, in a more preferred aspect the concentration is no lower than 200 µM. Typically, the lowest concentration is from 150 µM to 1.3 mM, from 200 µM to 1 mM, from 200 µM to 750 µM or from 200 µM to 500 µM. While the inventors have found that it is beneficial for the free concentration of silicate in the culture to remain above 150 µM during the culture, it is likely brief drops below this concentration would not greatly effect the ratio of EPA to ARA obtained. Therefore, brief drops below 150 µM of silicate concentration should not be considered to depart from this aspect of the invention. As shown in Table 7 and FIG. 1, ratios of EPA to ARA in the range of 11:1 to 13:1 can be achieved with no free silicate in the culture. However, above a concentration of 150 µM the ratio of EPA to ARA significantly increases. The most preferred maintained concentration of free silicate in the culture is in the range of 200-700 µM, more preferred is in the range 400-600 µM. The results as shown in FIG. 1 and Example 3, show a surprisingly high increase in the ratio of EPA to ARA at these most preferred concentration ranges.

This surprising result was unexpected and indicates the presence of a synergistic interaction between the components.

Most preferably, the nutrient solution comprises an initial concentration of organic carbon source of from 0.5 M to 10 M, a molar ratio of organic carbon to nitrogen of from 1 to 30, and a concentration of silicon in the form of silicate that falls no lower than 150 µM at any time.

In one option the culture is harvested continuously or discontinuously at an average rate such that, over time biomass is removed at the same rate at which it grows.

In a preferred option biomass is produced at a rate such that at least 5 mg EPA is produced per liter of culture per hour. In a more preferred option at least 10 mg EPA is produced per liter of culture per hour.

In another preferred option EPA forms at least 1.5% of the dry cell weight of the biomass. In a more preferred option EPA forms at least 2% of the dry cell weight of the biomass, in an even more preferred option EPA forms at least 3% of the dry cell weight of the biomass In a related aspect the invention provides a process for producing lipid mixtures and fatty acid mixtures derived from a culture as previously described in this section, wherein the mixtures are obtained by a harvesting process including the steps of:
- harvesting cells from the culture medium;
- optionally, heat or otherwise killing the cells to denature endogenous enzymes;
- forming the cells into a cake of biomass;
- optionally drying the biomass to reduce or eliminate water;
- extracting the cake of biomass with a non-selective lipid solvent and recovering the extracted material from the solvent as a residue (use of near critical di-methyl ether is one option, use of ethanol is another);
- optionally treating the extracted material with acids, alkalis and/or enzymes in the presence of an alcohol or water to form fatty acid or fatty acid alkyl ester mixtures; and
- optionally further concentrating and purifying said mixtures in order to achieve a required standard of purity.

EXAMPLES

The following general experimental techniques were employed:

Biomass Dry Weight Determination

Biomass dry weight is measured, using a pre-weighed glass fibre filter method as follows. A 10 ml sample is removed from a larger representative sample taken whilst stirring to achieve a broadly homogenous dispersion of cells and cell aggregates. The 10 ml sample is placed in a centrifuge tube and spun at 3000 rpm in a Heraeus Sepatech Megafuge 1.0 with swing-out rotor for 4 min and the liquid decanted leaving a cell pellet. The cell pellet is washed with phosphate-buffered saline and re-centrifuged. A Sartorius glass fibre filter is washed by passing 100 mL of deionised water through the filter then placing it in an oven at 60° C. for two hours prior to being weighed. The 10 ml sample is passed through the preweighed filter in a vacuum filter apparatus, washed with 50 mL deionised water and is then placed in an oven at 60° C. for two hours prior to being reweighed. The difference in grams between the pre and post weights times 100 is taken as a measure of the dry weight per liter.

Harvesting and Extraction of Lipid-Containing Material

Cells are harvested and washed to remove excess media. The wet equivalent of 0.75 g dry cell weight of cellular material is used to produce cellular extract. Cellular extract containing the lipids can be obtained by Folch extraction following the method of Bligh and Dyer (1959).

Total Fatty Acid Analysis

Total fatty acid analyses of samples of cellular extract are obtained to identify the composition of the cultured material. Addition of an internal standard such as C23:0 to the reaction allows measurement of the total fatty acid content of the cells. The method of fatty acid production entails a basic transesterification with 0.5 M methoxide in methanol followed by an acidic transesterification using dry HCl in methanol. Fatty acid methyl esters are recovered by extracting with hexane and drying with sodium sulphate before analysis using gas chromatography. The sample is run on a 30 m×0.25 mm ID Famewax (crossbond polyethylene glycol) glass capillary column contained within a Shimadzu 2010 GC by autoinjection. Fatty acids are identified by comparing the retention times of peaks under standard running conditions with those of known standards supplied by Sigma Aldrich.

Calculation of Nutrient Ratios

To allow comparisons of media with different carbon and nitrogen sources, the nutrient ratios within the media are reduced to molar ratios of the constituent atoms, for example one mol of glucose contains 6 mol carbon whereas 1 mol acetic acid contains only 2 mol carbon.

For the purposes of these calculations, the molecular weight of glucose is 180.16 such that 100 g of glucose contains 6×100/180.16 mol carbon.

For the purposes of these calculations, yeast extract is assumed to have a total nitrogen content of at least around 10% (w/w) so that 100 g yeast extract contains at least around (10/100)×100/14 mol nitrogen. Similarly tryptone has a nitrogen content of at least around 13% (w/w).

For the purposes of these calculations, yeast extract and tryptone are assumed to contribute a negligible amount of carbon as an energy source.

Molar nitrogen content from nitrates, and molar silicon content from silicates can be calculated directly using the molecular weight of each compound.

Example 1

3 g (dry weight) of a *Nitzschia laevis* strain In1 culture was transferred into a stirred tank fermenter with a working volume of 19.4 L. The vessel contained growth media with salts and vitamins as detailed in table 1 together with nutrients at concentrations of: 30 g/L glucose, 1.2 g/L yeast extract, 1.3 g/L sodium nitrate, 40 mg/L potassium dihydrogen phosphate and 270 mg/L sodium metasilicate pentahydrate.

TABLE 1

| Salt and vitamin content of fermenter media | |
| --- | --- |
| NaCl | 136.9 mM |
| MgSO4*7H2O | 8.9 mM |
| KCl | 7.2 mM |
| CaCl2 | 0.9 mM |
| (NH4)6Mo7O24*4H2O | 2.2 µM |
| CoCl2*6H2O | 1.0 µM |
| MnCl2*4H2O | 12.6 µM |
| Na2MoO4*2H2O | 1.0 µM |
| H3BO3 | 4.9 µM |
| ZnCl2 | 22.8 µM |
| FeCl3•6H2O | 8.1 µM |
| Na2EDTA | 72.5 µM |
| Vitamin B12 | 60 mg/L |
| Thiamine | 100 mg/L |
| Biotin | 100 mg/L |

The culture was aerated with one vessel volume of sterile air per minute and agitation controlled to give a dissolved oxygen content of >50%. pH was maintained at 8.0 by the addition of 0.4 N NaOH. Temperature was maintained at 20° C. by the circulation of hot or cold water through a jacket around the fermenter vessel as required.

Attached to the reactor was a settling device designed to separate media from cells. Culture was pumped into the device and cells were returned to the main fermenter vessel whilst spent media could be drawn off to waste. Fresh sterile media of the same composition as the initial medium was added to the fermenter vessel to keep the vessel volume constant at 19.4 L.

The amount of media removed to waste was increased gradually over the growth period until 19.4 L of media was being removed over a 24 hour period when the culture density reached the harvest density of around 10.5 g/L dry weight.

Once the culture reached harvest density, culture containing algal cells was bled off as harvest at a rate whereby the dry weight of the culture was kept between 10 and 11 g/L. The volume of spent media removed to waste was adjusted to keep the total volume removed from the reactor per day constant at 19.4 L. The volume removed from the fermenter was replaced with fresh media with the same composition as the initial media.

A steady state was reached where the cell density, harvest and composition remained stable. Glucose concentration in the waste media was greater than 5 g/L indicating that the cells were not carbon-limited.

The nutrient content of the fresh media input into the vessel was then changed so that it contained 2.1 g/L sodium nitrate, and 80 mg/L potassium dihydrogen phosphate with all other components remaining at their previous levels.

The continuous culture was maintained for a further 48 hours to allow the cells to adjust to the new nutrient levels. During this time the harvest rate required to maintain the same culture dry weight increased approximately 25% indicating that the culture had a higher growth rate when a higher level of nitrogen and/or phosphate was provided, indicating the culture had previously been nitrogen and/or phosphate limited. Glucose concentration in the waste media remained greater than 5 g/L indicating that the cells were again not carbon-limited.

Sterile samples of biomass were obtained from the cultures both prior to the nutrient change and post the change, and lipids extracted therefrom. Fatty acid profiles and ratios of components within the extract are shown in table 2 showing how the change in culture conditions has resulted in an improvement in composition with regard to the EPA:ARA ratio and an improvement in the ratio of EPA to co-concentrating components. EPA formed 2.3% of dry cell weight post the nutrient change.

Further increases in the sodium nitrate content of the media subsequent to this sample did not produce a marked increase in growth rate indicating that the culture was no longer nitrogen limited.

TABLE 2

Fatty acid percentages and ratios of culture before and after change in nutrient conditions. Percentages of fatty acids present are gives as a percentage of the total fatty acid content (w/w). Note that for simplicity fatty acids with 16 or less carbons have not been included in the table where they contribute less than 1% of total fatty acids. Where fatty acids of 18 carbons or more have been omitted from the table they have not been detected. In particular, no juniperonic acid or sciadonic acid could be detected.

| Compound Name | Pre nutrient change % of TFA (w/w) | Post nutrient change % of TFA (w/w) |
|---|---|---|
| C14:0 | 6.37 | 5.57 |
| C16:0 | 22.56 | 22.81 |
| C16:1n7 | 39.70 | 34.46 |
| C16:2n4 | 1.49 | 3.57 |
| C18:0 | 0.23 | 0.23 |
| C18:1n9 | 1.82 | 1.41 |
| C18:1n7 | 0.24 | 0.23 |
| C18:2n6 | 1.99 | 1.61 |
| C18:3n6 | 0.56 | 0.58 |
| C18:3n3 | 0.11 | 0.12 |
| C18:4:n3 | 0.75 | 1.37 |
| C20:2 | 0.07 | |
| C20:3n6 (DGLA) | 0.12 | 0.09 |
| C20:4n6 (ARA) | 2.14 | 1.44 |
| C20:4n3 (ETAn3) | 0.16 | 0.24 |
| C20:5n3 (EPA) | 16.00 | 19.43 |
| C22:2 | 0.44 | 0.41 |
| C22:5n3 (DPA) | 0.25 | 0.33 |
| C24:0 | 0.69 | 0.75 |
| C22:6n3 (DHA) | 1.02 | 1.30 |
| EPA:ARA | 7.5:1 | 13.5:1 |
| EPA: co-concentrating FAs | 7.8:1 | 8.2:1 |

TABLE 3

Molar ratios of carbon to nitrogen in nitrogen limiting and non-limiting media.

| | mol Carbon from Glucose | mol N from Yeast Extract | mol N from Sodium nitrate | Total mol N | Molar Ratio C:N |
|---|---|---|---|---|---|
| Before nutrient change | 1.0 | 0.00857 | 0.01530 | 0.023867 | 41.9:1 |
| After nutrient change | 1.0 | 0.00857 | 0.02471 | 0.033280 | 30.0:1 |

Example 2

3 g (dry weight) of a *Nitzschia laevis* strain In1 culture was transferred into a stirred tank fermenter with a working volume of 18 L. The vessel contained growth media with salts and vitamins as detailed in table 1 together with nutrients at concentrations of: 30 g/L glucose, 1.6 g/L yeast extract, 2.98 g/L sodium nitrate, 80 mg/L potassium dihydrogen phosphate and 270 mg/L sodium metasilicate pentahydrate.

The culture was aerated with one vessel volume of sterile air per minute and agitation controlled to give a dissolved oxygen content of >50%. pH was maintained at 8.0 by the addition of 0.4 N NaOH. Temperature was maintained at 20° C. by the circulation of hot or cold water through a jacket around the fermenter vessel as required.

Attached to the reactor was a settling device designed to separate media from cells. Culture was pumped into the device and cells were returned to the main fermenter vessel whilst spent media could be drawn off to waste. Fresh sterile media was added to the fermenter vessel to keep the vessel volume constant at 18 L. The media contained salts as per table 1 together with nutrients at concentrations of: 30 g/L glucose, 1.6 g/L yeast extract, 2.98 g/L sodium nitrate, 80 mg/L potassium dihydrogen phosphate and 530 mg/L sodium metasilicate pentahydrate. The media contained a molar ratio C:N of less than 30:1 (see table 5) so as to avoid nitrogen limitation.

The amount of media removed to waste was increased gradually over the growth period until 18 L of media was being removed over a 24 hour period when the culture density reached the harvest density of around 10 g/L dry weight.

Once the culture reached harvest density, culture containing algal cells was bled off as harvest at a rate whereby the dry weight of the culture was kept between 10 and 11 g/L. The volume of spent media removed to waste was adjusted to keep the total volume removed from the reactor per day constant at 18 L. The volume removed from the fermenter was replaced with fresh media with the same composition as the initial media.

A steady state was reached where the cell density, harvest and composition remained stable. At this point 6.1 g dry cell weight was being harvested per 24 hours per liter of culture. At a silicate requirement of around 325 µmol per g dry weight the daily silicate requirement for biomass synthesis was 1986 µmol $L^{-1}$ day$^{-1}$. Silicate provision was at 2491 µmol $L^{-1}$ day$^{-1}$ giving an excess Si concentration of 505 µmol. Sterile samples of biomass were obtained from the culture and lipids extracted therefrom. A fatty acid profile and ratios of components within the extract are shown in table 4. EPA formed 2% of dry cell weight under these conditions leading to an EPA yield rate of 5.1 mg EPA per liter of culture per hour.

TABLE 4

Percentage of fatty acids present as a percentage of the total fatty acid content (w/w). Fatty acid ratios and percentages of culture during steady state. Note that for simplicity fatty acids with 16 or less carbons have not been included in the table where they contribute less than 1% of total fatty acids. Where fatty acids of 18 carbons or more have been omitted from the table they have not been detected.

| Compound Name | % of TFA (w/w) |
|---|---|
| C14:0 | 4.78 |
| C16:0 | 25.56 |
| C16:1n7 | 28.98 |
| C16:2n4 | 5.48 |
| C18:0 | 0.26 |
| C18:1n9 | 1.10 |
| C18:1n7 | N.D. |
| C18:2n6 | 1.66 |
| C18:3n6 | 0.70 |
| C18:3n3 | 0.10 |
| C18:4:n3 | 1.92 |
| C20:2 | 0.11 |
| C20:3n6 (DGLA) | 0.11 |
| C20:4n6 (ARA) | 1.42 |
| C20:4n3 (ETAn3) | 0.27 |
| C20:5n3 (EPA) | 21.07 |
| C22:2 | 0.43 |
| C22:5n3 (DPA) | 0.32 |
| C24:0 | 1.13 |
| C22:6n3 (DHA) | 1.40 |

TABLE 4-continued

Percentage of fatty acids present as a percentage of the total fatty acid content (w/w). Fatty acid ratios and percentages of culture during steady state. Note that for simplicity fatty acids with 16 or less carbons have not been included in the table where they contribute less than 1% of total fatty acids. Where fatty acids of 18 carbons or more have been omitted from the table they have not been detected.

| Compound Name | % of TFA (w/w) |
|---|---|
| EPA:ARA | 14.8:1 |
| EPA: co-concentrating FAs | 8.0:1 |

N.D.—not detected.

TABLE 5

Molar ratio of carbon to nitrogen in media.

| mol Carbon from Glucose | mol N from Yeast Extract | mol N from Sodium nitrate | Total mol N | Molar Ratio C:N |
|---|---|---|---|---|
| 1.0 | 0.01143 | 0.03506 | 0.04649 | 21.5:1 |

Example 3

3 g (dry weight) of a *Nitzschia laevis* strain In1 culture was transferred into a stirred tank fermenter with a working volume of 14 L. The vessel contained growth media with salts and vitamins as detailed in table 1 together with nutrients at concentrations of: 50 g/L glucose, 1.9 g/L yeast extract, 4.0 g/L sodium nitrate, and 170 mg/L potassium dihydrogen phosphate. Sodium metasilicate pentahydrate was added separately as a concentrated stock to a concentration of 143 mg/L.

The culture was aerated with one vessel volume of sterile air per minute and agitation controlled to give a dissolved oxygen content of >50%. pH was maintained at 8.0 by the addition of 0.4 N NaOH. Temperature was maintained at 20° C. by the circulation of hot or cold water through a jacket around the fermenter vessel as required.

The media contained a molar ratio C:N of less than 30:1 (see table 6) so as to avoid nitrogen limitation. All measurements of levels in harvested media confirmed that there was ≥80 mg/L nitrate in the culture. Since the fermenter is refilled with fresh media immediately after harvest, this measurement represents the lowest nitrate concentration in the fermenter and so nitrogen was not limiting throughout this example.

TABLE 6

Molar ratio of carbon to nitrogen in media.

| mol Carbon from Glucose | mol N from Yeast Extract | mol N from Sodium nitrate | Total mol N | Molar Ratio C:N |
|---|---|---|---|---|
| 1.665 | 0.013571 | 0.047064 | 0.060636 | 27.5:1 |

Once the culture reached harvest density, culture containing algal cells was harvested at six-hourly intervals at a variable volume whereby the dry weight of the culture was kept around 7.5 g/L. The volume removed from the fermenter was replaced with fresh media with the same glucose, sodium nitrate, yeast extract and potassium dihydrogen phosphate content as the initial media.

Silicon as a concentrated aqueous solution of sodium metasilicate was added independently of other media and was added at regular intervals throughout the day rather than all at the time of media refill in order to avoid problems of precipitation at high concentration. The frequency of sodium metasilicate addition was altered to vary the concentration of silicon in the culture medium.

Samples were taken for fatty acid analysis at daily intervals and the EPA:ARA ratio within the biomass calculated.

Available sodium metasilicate levels in the fermenter were calculated by taking the residual silicate levels, adding the amount of silicate added, subtracting the amount incorporated into biomass (at 325 µmol silicon per g dry weight) and compensating for the dilution caused when the fermenter harvested and refilled with silicate-free media.

The results as shown in table 7 and FIG. 1 show a strong correlation between available silicate and EPA:ARA ratio with EPA:ARA remaining below 14:1 in all cases where silicate levels in the culture became limited (i.e. fell to zero). Surprisingly, a ratio of greater than 14:1 was not seen until the minimum level of sodium metasilicate was above 150 µM.

For all samples where measurements were taken (samples 3 to 11 in table 7) EPA formed at least 3% of the dry weight of the biomass.

TABLE 7

EPA:ARA ratios in biomass formed in media with different minimum sodium metasilicate concentrations.

| Sample | Minimum sodium metasilicate concentration (µM) | EPA:ARA ratio |
|---|---|---|
| 1 | 213 | 14.3:1 |
| 2 | 0 | 13.0:1 |
| 3 | 0 | 12.2:1 |
| 4 | 0 | 11.6:1 |
| 5 | 142 | 12.9:1 |
| 6 | 193 | 14.1:1 |
| 7 | 569 | 20.1:1 |
| 8 | 690 | 19.0:1 |
| 9 | 507 | 21.6:1 |
| 10 | 476 | 23.6:1 |
| 11 | 496 | 22.6:1 |

Example Four

Biomass was produced according to the method above and lipids extracted from freeze dried biomass. The lipids were converted to free fatty acids using KOH in 2:1 ethanol:water, dried to remove water, and then converted to ethyl esters using $H_2SO_4$ in ethanol.

The resulting ethyl esters were concentrated according to the methods disclosed by W. B. Nilsson ("Supercritical Fluid Technology in Oil and Lipid Chemistry" Editors J. W. King & G. R. List, AOCS Press, ISBN0-935315-T1-3, 1996, pp. 180-212). The concentrations of fatty acids with 20 carbons or more before and after concentration are shown in table 8.

Note that, whilst the relative proportions of each of these fatty acids has increased several fold, the ratio of EPA to ARA has only changed slightly, thus demonstrating the advantage of generating starting material with a high ratio of EPA to ARA.

TABLE 8

Fatty acids with 20 carbons or more before and after concentration.

| Fatty Acid | Proportion of total fatty acids prior to concentration (%) | Proportion of total fatty acids after concentration (%) |
|---|---|---|
| C20:3 n-6 | <0.1 | <0.1 |
| C20:4 n-6 (ARA) | 1.74 | 3.85 |
| C20:4 n-3 | 1.45 | 3.15 |
| C20:5 n-3 (EPA) | 26.74 | 71.0 |
| C22:5 n-3 | 0.51 | 1.35 |
| C24:0 | <0.1 | <0.1 |
| C22:6 n-3 | 1.98 | 7.4 |
| EPA:ARA | 15.4:1 | 18.4:1 |

Example Five

*Mortierella renispora*, a fungus of the genus *Mortierella*, is cultured heterotrophically under conditions chosen to produce biomass with a fatty acid composition comprising a ratio of EPA to ARA of about 11:1 or more and a ratio of EPA to total co-concentrating fatty acids of about 8:1 or more. The biomass is harvested and the lipids extracted. The extracted lipids are transesterified to form ethyl esters. The ethyl esters are then processed to produce a fatty acid ethyl ester concentrate in which EPA forms at least 60% of the total fatty acids by weight, and this concentrate is then purified to produce an EPA ethyl ester of over 90% purity.

Example Six

*Chlorella minutissima*, an alga of the genus *Chlorella*, is cultured heterotrophically under conditions chosen to produce biomass with a fatty acid composition comprising a ratio of EPA to ARA of about 11:1 or more and a ratio of EPA to total co-concentrating fatty acids of about 8:1 or more. The biomass is harvested and the lipids extracted. The extracted lipids are transesterified to form ethyl esters. The ethyl esters are then processed to produce a fatty acid ethyl ester concentrate in which EPA forms at least 60% of the total fatty acids by weight, and this concentrate is then purified to produce an EPA ethyl ester of over 90% purity Example Seven

*Nannochloropsis oceanica*, an alga of the genus *Nannochloropsis*, is cultured heterotrophically under conditions chosen to produce biomass with a fatty acid composition comprising a ratio of EPA to ARA of about 11:1 or more and a ratio of EPA to total co-concentrating fatty acids of about 8:1 or more. The biomass is harvested and the lipids extracted. The extracted lipids are transesterified to form ethyl esters. The ethyl esters are then processed to produce a fatty acid ethyl ester concentrate in which EPA forms at least 60% of the total fatty acids by weight, and this concentrate is then purified to produce an EPA ethyl ester of over 90% purity.

Example Eight

A screen is carried out after the method of Barclay (U.S. Pat. No. 5,130,242) to identify a *Thraustochytrid* sp. in which the level of EPA as a percentage of total fatty acids is high relative to the proportion of ARA and co-concentrating fatty acids. The microorganism is then grown under heterotrophic conditions chosen to produce biomass with a fatty acid composition comprising a ratio of EPA to ARA of about 11:1 or more and a ratio of EPA to total co-concentrating fatty acids of about 8:1 or more. The biomass is harvested and the lipids extracted. The extracted lipids are transesterified to form ethyl esters. The ethyl esters are then processed to produce a fatty acid ethyl ester concentrate in which EPA forms at least 60% of the total fatty acids by weight, and this concentrate is then purified to produce an EPA ethyl ester of over 90% purity.

Example Nine

*Cyclotella cryptica*, a diatom, is cultured heterotrophically under conditions chosen to produce biomass with a fatty acid composition comprising a ratio of EPA to ARA of about 14:1 or more. The biomass is harvested and the lipids extracted. The extracted lipids are transesterified to form ethyl esters. The ethyl esters are then processed to produce a fatty acid ethyl ester concentrate in which EPA forms at least 60% of the total fatty acids by weight, and this concentrate is then purified to produce an EPA ethyl ester of over 90% purity.

Example Ten

*Phaeodactylum tricornutum*, a diatom that is an obligate photoautotroph, is transformed according to the method of Apt et al. (U.S. Pat. No. 7,939,710) to give it the ability to grow heterotrophically using glucose as a source of energy and carbon. The transformed organism is cultured heterotrophically under conditions chosen to produce biomass with a fatty acid composition comprising a ratio of EPA to ARA of about 14:1 or more. The biomass is harvested and the lipids extracted. The extracted lipids are transesterified to form ethyl esters. The ethyl esters are then processed to produce a fatty acid ethyl ester concentrate in which EPA forms at least 60% of the total fatty acids by weight, and this concentrate is then purified to produce an EPA ethyl ester of over 90% purity.

GENERAL

The examples therefore show compositions (including microbial biomass and fatty acid compositions) containing in the region of (or greater than) 20% EPA by weight of total fatty acids, with a ratio of EPA to ARA of 11:1 or greater, and with a ratio of EPA to co-concentrating fatty acids of 8:1 or greater. The compositions have also been shown to be able to be purified to greater than 70% EPA by weight of total fatty acids, while at least retaining the ratio of EPA to ARA in the composition.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Wherein the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention as claimed.

The invention claimed is:

1. A method of producing a diatom, the method comprising:
   a. cultivating diatoms in heterotrophic culture containing a nutrient solution comprising:
      (i) a nitrogen source and an organic carbon source at an initial concentration of at least 0.5 M carbon,
      (ii) a molar ratio of organic carbon to nitrogen of no higher than 30:1 (mol C:mol N), and
      (iii) a non-limiting source of silicate at a concentration of 150 µM to 1.3 mM at all times during the culture; and
   b. recovering the diatom from the heterotrophic culture, wherein the cultivating conditions result in production of a diatom having at least 1.5% (w/w) of dry weight as eicosapentaenoic acid and an eicosapentaenoic acid to arachidonic acid ratio of at least 14:1.

2. The method of claim 1 wherein the diatoms are cultivated in heterotrophic culture in a fermenter.

3. The method of claim 2 wherein the cultivation comprises continuous fermentation.

4. The method of claim 1 wherein the diatoms comprise *Nitzschia* species.

5. The method of claim 1 wherein the cultivation is carried out at a temperature of from about 12° C. to about 35° C.

6. The method of claim 1 wherein the cultivation is carried out at a pH of from about 7.0 to about 8.7.

7. The method of claim 1 wherein said carbon source comprises glucose.

8. The method of claim 1 wherein said carbon source is selected from glucose, hydrolysed starch or hydrolysed whey.

9. The method of claim 1 wherein said nitrogen source is in the form of sodium nitrate or potassium nitrate.

10. The method of claim 1 wherein said nitrogen sources is supplemented with an amino-acid source.

11. The method of claim 10 wherein said amino-acid source is selected from corn-steep liquor, yeast extract, tryptone, peptones, lysine and glutamate.

12. The method of claim 1 wherein said silicate is in the form of sodium or potassium metasilicate.

13. The method of claim 1 wherein the nutrient solution comprises phosphorous in the form of phosphate.

14. The method of claim 13 wherein the molar ratio of organic carbon to phosphorus in the form of phosphate is no higher than 1250:1 (mol C:mol P).

* * * * *